United States Patent [19]
Goldman

[11] Patent Number: 5,510,621
[45] Date of Patent: Apr. 23, 1996

[54] APPARATUS AND METHOD FOR MEASURING COMPONENTS IN A BAG

[75] Inventor: Don S. Goldman, Folsom, Calif.

[73] Assignee: Optical Solutions, Inc., Folsom, Calif.

[21] Appl. No.: 317,114

[22] Filed: Oct. 3, 1994

[51] Int. Cl.$^6$ ........................................... G01J 3/02
[52] U.S. Cl. .............................. 250/343; 356/246
[58] Field of Search ........................ 250/343, 347, 250/353; 356/246, 409, 440, 442; 128/633

[56] References Cited

U.S. PATENT DOCUMENTS

| | | | |
|---|---|---|---|
| 3,690,769 | 9/1972 | Mori | 356/41 |
| 3,857,485 | 12/1974 | Frank | 206/305 |
| 3,924,128 | 12/1975 | Frank | 250/328 |
| 4,800,279 | 1/1989 | Hieftje et al. | 250/339 |
| 4,872,868 | 10/1989 | Chevallier | 604/327 |
| 5,002,397 | 3/1991 | Ingrum et al. | 356/407 |
| 5,186,057 | 2/1993 | Everhart | 73/861.41 |
| 5,239,860 | 8/1993 | Harris et al. | 73/61.48 |

OTHER PUBLICATIONS

"Simple Methods For The Quantitative Determination of Procaine Hydrochloride In Parenteral Products" by Das Gupta et al., pp. 408–410, Dated Jul. 1969.

"Nondestructive NIR and NIT Determinatin Of Protein, Fat, And Water In Plastic Wrapped, Homogenized Meat" by Tomas Isaksson et al., pp. 1685–1694, Dated 1992.

"Near Infrared Multi-Component Analysis of Parenteral Products Using The InfraAlyzer 400" by John J. Rose, 71–78, Dated Mar.–Apr. 1982.

"The Spectrophotemetric Absorbance of Intralipid" by Cane et al., pp. 53–55, Dated 1980.

*Primary Examiner*—Davis L. Willis
*Assistant Examiner*—Richard Hanig
*Attorney, Agent, or Firm*—Bielen, Peterson & Lampe

[57] ABSTRACT

An apparatus for measuring components in a liquid medium, in particular parenteral nutrients, within a flexible transparent bag. A spacer is utilized to fix or determine the optical path across the bag chamber and includes a passage for electromagnetic radiation of selected wavelengths. The source of electromagnetic radiation is capable of sending radiation into the bag chamber and to detector means which analyzes the radiation passed through or reflected from the components in the bag chamber.

21 Claims, 7 Drawing Sheets

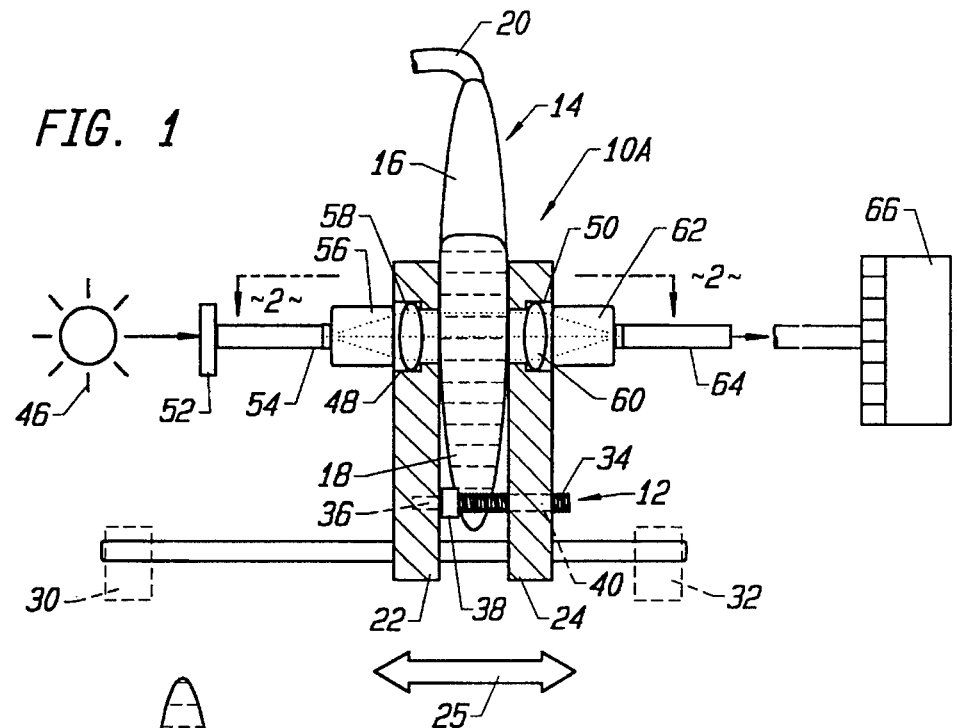
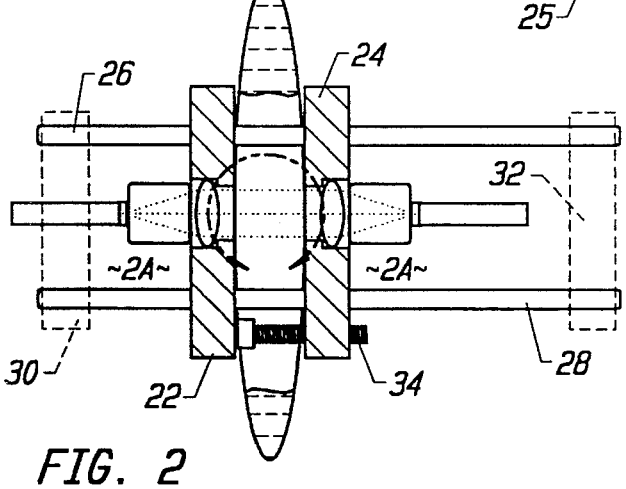
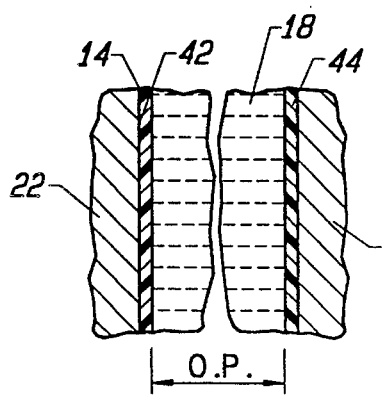
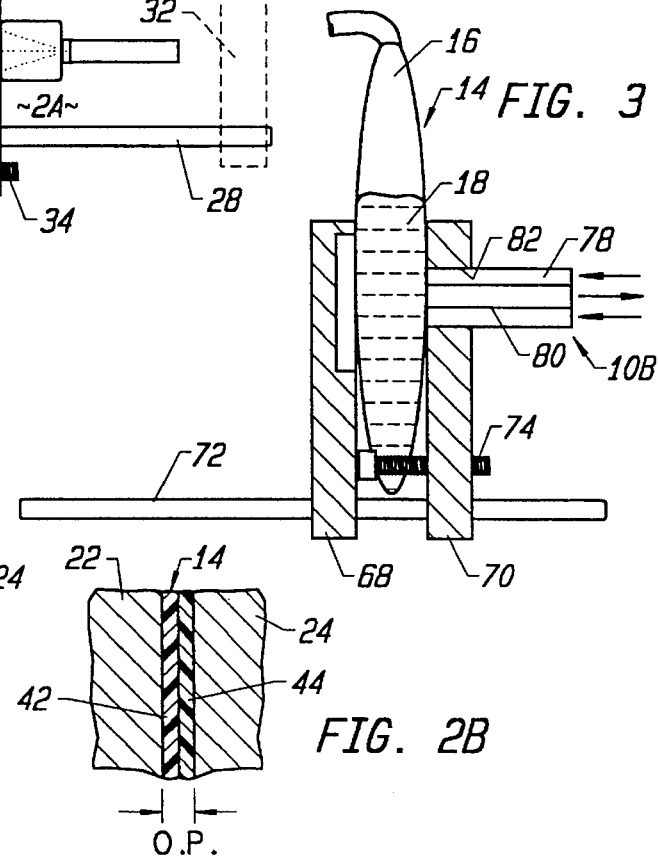

APPARATUS AND METHOD FOR MEASURING COMPONENTS IN A BAG

BACKGROUND OF THE INVENTION

The present invention relates to a novel and useful apparatus and method for non-invasively analyzing liquid medium components in a bag.

Liquid compounds are often placed in bags for various purposes. For example, the use of total parenteral nutrients (TPN), which are eventually the source of intravenous feeding, are stored in transparent or translucent flexible bags. TPN compounds are commonly mixed in pharmacies using commercially available compounders which accept three or more TPN compounds and automatically mix these compounds into an appropriate container such as an intravenous (I.V.) bag. Intravenous use of the bags usually takes place at a later time in a hospital or medical facility. Typical compounds include 70% dextrose injection U.S.P., 10% Travasol (amino acid) injection, Intralipid 20% fat I.V. emulsion, sterile water, and many others.

Presently, methods such as color coding are relied upon to avoid making errors during the compounding or mixing process. Namely, different tubes feeding the I.V. bag possess connectors of different colors which correspond to the colors of the specific mixing positions on the compounder. For example, setting a red indicator on a compounder for 100 milliliters would deliver 100 milliliters from a starting bottle connected to the tubing line which possesses red connectors. However, there is no assurance that the correct compound was initially connected to the red tubing line. Consequently, an incorrect connection of the tubing between bottles of dextrose solution and water, for example, may have dire consequences, such as death for patients with sugar intolerance.

Many of the TPN compounds are clear liquids. That is to say, water, amino acid injection, dextrose injection, and electrolytes are clear liquids precluding visual distinction among them. Furthermore, it is preferable to perform identification of TPN components non-invasively and rapidly to minimize potential contamination and to minimize analysis time by personnel.

An article entitled *"Near Infrared Multi-Component Analysis of Parenteral Products Using the InfraAlyzer 400,"* by Rose et al. examined meglumine and meglumine diatrizoate in 30% diatrizoate meglumine injections solutions using diffuse reflectance in the near infrared region. The best combinations of three or four wavelength filters from nineteen (19) available wavelength filters were selected using multiple regression statistical methods. The specific wavelengths were not identified.

An article entitled *"The Spectrophotometric Absorbance Of Absorbance of Intralipid"* by Carne et al. develops calibrations for Intralipid in water in concentrations from 2.5 to 40 mg/ml at six (6) visible wavelengths between 505 and 626.6 nanometers. Intralipid interferes with spectrophotometric analysis of oxyhemoglobin, carboxyhemoglobin, and total hemoglobin.

A writing entitled, *Simple Methods For Quantitative Determination of Procaine Hydrochloride In Parenteral Products* by Das Gupta et al. presents calibrations in the ultraviolet region of spectrophotometry. Specifically, the Das Gupta reference obtained calibrations at 228 nanometers for buffered solutions of procaine hydrochloride in the 0–20 microgram/ml concentration range.

An article entitled *"Nondestructive NIR and NIT Determination Of Protein, Fat, And Water In Plastic-Wrapped, Homogenized Meat"* by Isaksson et al., describes NIR measurements of proteins by diffuse reflectance in meat samples with and without plastic coatings. Samples were placed in a rubber cup prior to covering the meat sample with plastic laminant.

U.S. Pat. Nos. 4,800,279 and 5,002,397 describe methods and devices for visible and near-infrared evaluation of physical properties of samples.

U.S. Pat. No. 4,872,868 shows an analyzer for collection bags which provides an envelope that permits the insertion of reagent's test strips and the like.

U.S. Pat. Nos. 3,857,485 and 3,924,128 teach a method of analyzing sample containers by liquid scintillation spectrometry which utilizes light transmission sealing means to prevent entry of ambient light or the escape of light from the photomultiplier tube detection devices.

U.S. Pat. No. 5,239,860 describes a sensor for continuously measuring alcohol and gasoline fuel mixtures in a clear Teflon tube using a pre-determined optical path and electromagnetic radiation at a pair of wavelengths which are generated by rapidly switching currents through a lightsource. Thermopile detectors are used to detect an increase in temperature due to light transmitted through the flowing gasoline/alcohol mixture.

An apparatus and method for identifying solutions in a translucent transparent or semi-transparent plastic bag, such as parenteral nutrients, non-invasively, qualitatively and quantitatively would be a notable advance in the chemical analysis field.

SUMMARY OF THE INVENTION

In accordance with the present invention a novel and useful apparatus and method for identifying parenteral nutrients is herein provided.

The apparatus of the present invention employs spacer means for supporting a flexible transparent or translucent bag and for determining the optical patch across the bag chamber. The spacer means includes a passage for electromagnetic radiation. The spacer means may take the form of a pair of rigid elements or fences and a mechanism for shortening or lengthening the distance between the rigid fences. The rigid fences may support the bag against vertical movement and also be capable of exerting compressive force on the bag to a precisely determined dimension between the rigid fences. Such dimension would correspond to a particular optical path, which may include the bag wall alone or the bag wall and the bag filled with components in a liquid medium.

A source of electromagnetic radiation directs electromagnetic radiation through the spacer passage and to the wall portion of the bag. The source of electromagnetic radiation may produce coherent light, ultraviolet radiation, x-rays, infrared radiation, broad band radiation e.g., a tungsten source, and the like.

Detector means is also employed in the present invention for analyzing the electromagnetic radiation passed through the spacer passage and along a determined optical path which is through a dimension of the bag chamber. In certain cases the optical path may pass completely across the bag such that the detector is receiving light which has been transmitted through the bag. In other cases, the detector may be placed on the same side of the bag as the source of electromagnetic radiation and receive light which has interacted with the contents of the bag by diffuse reflectance. Further, the detector may receive light by diffuse reflectance and/or by diffuse transflectance, i.e., where light passes through the bag and then is reflected back through the bag by a diffuse reflector or mirror located on the opposite side of the bag relative to the detector. It has been found that near-infrared radiation is particularly useful in detecting parenteral nutrients in a flexible I.V. bag. In addition, specific wavelengths, rather than a continuum of wavelengths, may be used as the radiation sought for analysis to enable the use of simpler and less expensive instrumentation comprised of several discrete detectors, each covered by a narrow wavelength filter. Fiber optics may also be utilized to carry light to and from the I.V. bag. Mathematical models may be employed to quantitatively and qualitatively detect components within the I.V. bag accurately and quickly.

Another adaption of the device of the present invention produces a self referencing device with respect to the intensity. Specifically, transmittance measurements may be taken of the bag alone, squeezed to eliminate a chamber and to expel the liquid components, and along a determined optical path of the bag filled with certain components. Absorbance for a sample may be accurately determined under the Beer's Law relationship. Chemical concentration can be directly related to an absorbance difference obtained from a spectral measurement using two different path lengths. This technique minimizes or eliminates common spectroscopic measurement problems due to contamination, changes in the spectroscopic windows holding the sample, instrument problems due to temperature changes on internal optical elements, the source of electromagnetic radiation, and the like.

It may be apparent that a novel and useful apparatus for analyzing components in a liquid medium has been described.

It is therefore an object of the present invention to provide an apparatus and method for analyzing liquid components in a flexible transparent or translucent container or without invading the integrity of the bag.

Another object of the present invention is to provide a method and apparatus for analyzing components in a liquid medium within a flexible transparent or translucent container to prevent misuse of such components in treating patients in a medical facility.

A further object of the present invention is to provide a method and apparatus for analyzing components in a liquid medium found in a transparent or translucent plastic container which is accurate and may include qualitative as well as quantitative measurements of the components therein.

A further object of the present invention is to provide a method and apparatus for analyzing components in a liquid medium found in a transparent or translucent flexible bag where such components are parenteral or enteral nutrients typically used for intravenous feeding.

A further object of the present invention is to provide a method and apparatus for analyzing components in a liquid medium found in a translucent flexible bag which is capable of detecting light from a source after interaction with the bag alone and after interaction with the bag and the components in the bag.

Another object of the present invention is to provide a method and apparatus for analyzing components in a liquid medium within a flexible bag employing either transmittance or diffuse reflectance techniques.

The invention possesses other objects and advantages especially as concerns particular characteristics and features thereof which will become apparent as the specification continues.

BRIEF DESCRIPTION OF THE DRAWINGS

FIG. 1 is a sectional view of a first embodiment of the apparatus of the present invention.

FIG. 2 is a sectional view of the apparatus of FIG. 1 taken along line 2—2 of FIG. 1.

FIG. 2A is a sectional view taken along line 2A—2A of FIG. 2.

FIG. 2B is a sectional view of an I.V. bag collapsed by the apparatus of the present invention.

FIG. 3 is a side sectional view of another embodiment of the apparatus of the present invention.

Figure 4:
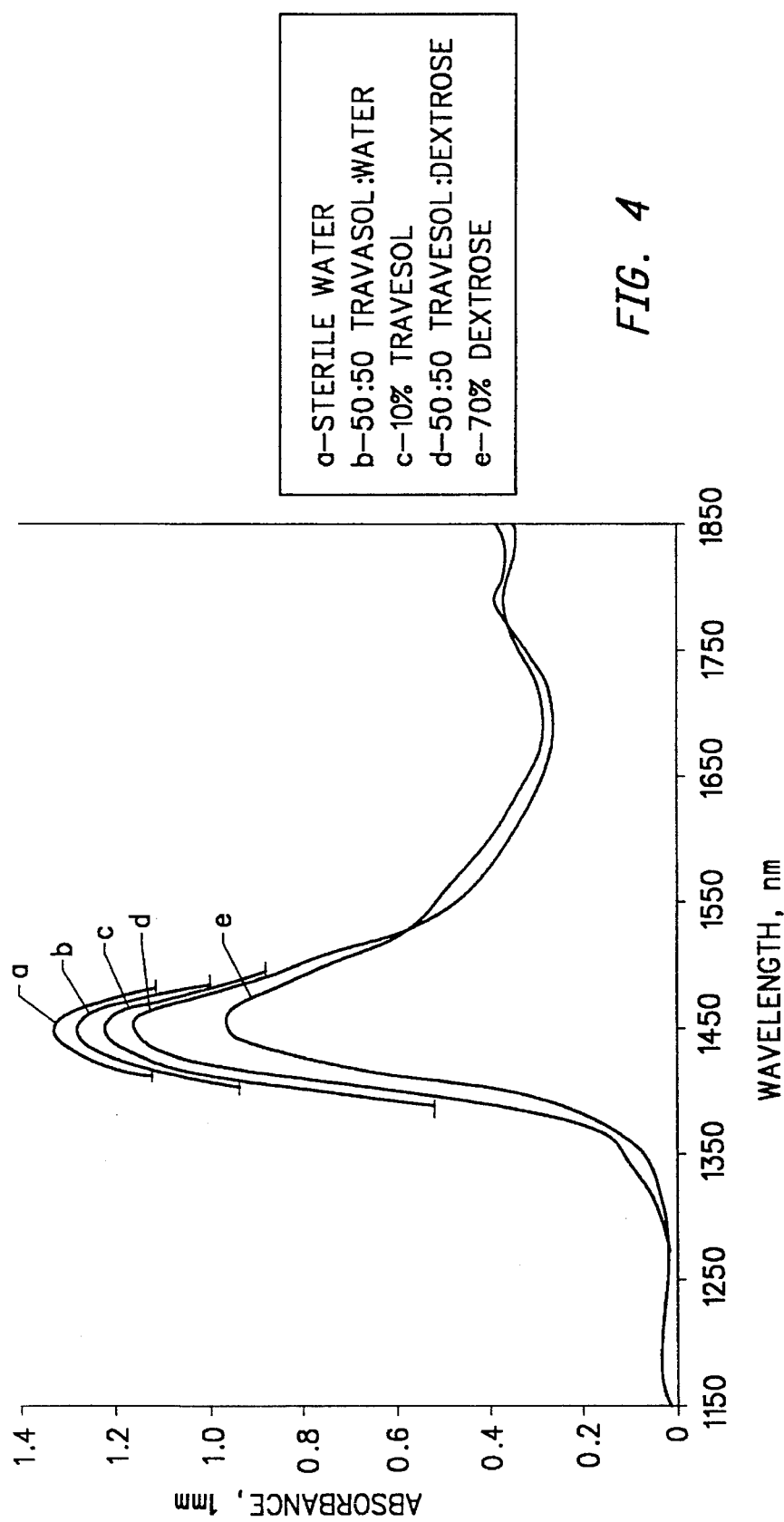
FIG. 4 is a graphical representation with experimental results described in Example 1.

For a better understanding of the invention reference is made to the following detailed description of the preferred embodiments which should be referenced to the herein before described drawings.

DETAILED DESCRIPTION OF THE PREFERRED EMBODIMENTS

Various aspects of the present invention will evolve from the following detailed description of the preferred embodiments thereof which should be taken in conjunction with the hereinbefore described drawings.

The invention as a whole is depicted in the drawings by reference character 10. The apparatus 10 is shown in the drawings as including multiple embodiments, denoted by the addition of an upper case letter. Referring to FIG. 1, apparatus 10A is depicted in which spacer means 12 is provided to hold a flexible transparent or semi transparent bag 14 in place. The term "translucent" is used herein to indicate a transparent, semi-transparent, or non-opaque bag. Bag 14 includes a chamber 16 which is capable of holding components in a liquid medium 18. Liquid medium including such components 18 are passed through tube 20, shown partially in FIG. 1, which is ultimately clamped or sealed when the bag 14 is filled. Bag 14 may take the form of a plastic intravenous bag (I.V. bag) formed of polyvinyl chloride (PVC), ethylene vinyl acetate (EVA), and like materials. However, other containers may be employed herein. The liquid medium and components 18 found within bag 14 may consist of mixtures of parenteral or enteral nutrients which may be intravenously fed to a patient. For example, such nutrients may include sterile water, 70% dextrose injection U.S.P., 10% Travasol (amino acid) Aminosyn or FreeAmine injection, Intralipid 20% fat I.V. emulsion, potassium chloride, and the like, individually or in various combinations.

Spacer means 12 includes a pair of elements 22 and 24 which are shown in FIGS. 1 and 2 as a pair of solid fences placed in opposition to one another. Fences 22 and 24 are slidingly supported by rods 26 and 28 which are supported to a surface by stands 30 and 32, depicted in phantom on FIGS. 1 and 2. Rods 26 and 28 serve as a guide for fences 22 and 24. A threaded screw 34 is fixed to fence 22 through a boss 36. Knurled wheel and bearing unit 38 is capable of turning relative to boss 36. The turning of wheel 38 also rotates threaded connect screw 34 which threadingly engages a threaded bore 40 through fence 24. Thus, fence 22 is stationary relative to rods 26 and 28 while fence 24 is moveable thereto, manually or by motor means, such as a solenoid, directional arrow 25. Unit 38 serves to measure or to stop the relative movement of fences 22 and 24, to determine the optical path through bag 14 or sequentially determine a plurality of optical paths through bag 14. It should be noted that fences 22 and 24 may be hingedly attached to one another to determine the distance therebetween, like a clamshell.

With reference to FIG. 2A, it maybe observed that such optical path (O.P.) of components 18 within bag 14 may be easily adjusted by the movement of fence 24 relative to fence 22. The O.P. may vary between 1.0 millimeter to 15 millimeters in many cases. In certain instances, an empty bag 14 may be compressed by fences 22 and 24 such that walls 42 and 44 touch one another, FIG. 2B, eliminating chamber 16. This configuration is useful in obtaining a reference value for the bag without medium 18 in chamber 16. Inner surfaces 42 and 44 of fences 22 and 24, respectively also provide sufficient friction to prevent the slippage of bag 14 downwardly between fences 22 and 24. Of course, other structures may be employed to prevent the slippage of bag 14 within spacer means 12 such as a floor, or suspension device pulling upwardly on bag 14 while bag 14 is within spacer means 12, and the like.

Apparatus 10 further possesses a source of electromagnetic radiation 46. Source 46 may take the form of laser light, infrared radiation, ultraviolet radiation, visible radiation, or any other electromagnetic radiation found in the spectrum. Light 46 is passed to bag chamber 16 through passage 48 in fence 22 and from chamber 16 of bag 14 through passage 50 of fence 24. Electromagnetic radiation from source 46 may be filtered by filter 52 and led to passage way 48 by optical fiber or fiber bundle 54. Fitting 56 directs radiation from fiber optical bundle 54 to collimating lens 58. Parallel rays of electromagnetic radiation are then passed through bag 14 and liquid medium 18 containing various components to converging lens 60. Fitting 62 directs the electromagnetic radiation through optical fiber or fiber optic bundle 64 to a detector 66 for analysis. Detector means 66 in its broadest sense may take the form of any suitable spectrophotometer, single or multiple detectors, or sources being appropriately filtered for the wavelength of interest, in combination with a computer employing an appropriate software program such as Gram 386, available from Galactic Industries, Inc. of Salem N.H.

With reference to FIG. 3, embodiment 10B of the present invention is depicted. Apparatus 10B possesses a pair of opposing elements or fences 68 and 70. As in embodiment 10A, guide 72 may take the form of a pair of rods supported by stands on a surface, a hinged clamshell configuration, or the like. Fence 68 is fixed to guide 72 while fence 70 is moved and the distance between fences 68 and 70 is set by threaded screws 74, in the same manner as threaded screw 34 found in embodiment 10A. Fence 68 includes a diffuse reflector 76 on one side of bag 14 containing liquid medium 18 having various components therewithin. Of course, diffuse reflector may be formed integrally with bag 14. Diffuse reflector 76 may take the form of a white ceramic disk or other suitable reflector. Light from source 46, not shown, passes through outer fiber or fiber bundle 78, from bag 14 containing a liquid medium having various components 18, and through fiber optic bundle 80, which is formed concentrically with fiber optic bundle 78. Analysis of the components within bag chamber 16 takes place by interaction of the electromagnetic radiation from fiber optic bundle 78 by diffuse reflectance, by diffuse transflectance, in conjunction with diffuse reflector 76, or a combination of both. The latter is especially useful where liquid medium is murky to an uncertain degree. Such diffuse reflectance measurements may be obtained simply by pressing an I.V. bag filled with light scattering material against fence 70 without the use of fence 68. Again, fiber optic bundles 78 and 80 may be angularly disposed with respect to each other i.e., 30 degrees, to minimize specular components of electromagnetic radiation reflected from bag 14.

The general operation of embodiments 10A and 10B takes place by supporting bag 14 within spacer means 12, which may include elements 22 and 24 of embodiment 10A, or fences 68 and 70 of embodiment 10B. Spacer means 12 is then adjusted to solely determine the desired optical path within bag 14 or to sequentially determine the optical path through a plurality of bags such as bag 14. In general, where liquid medium 18 is not perfectly clear, as in the case of lipids, the optical path would be short. For murky light scattering liquids, it is unlikely that radiation will reach the far side of bag 14 and be reflected back from diffuse reflector or mirror 76. In such a case, the space between fences 68 and 70 is not critical. The converse is true with clear liquid medium 18. Electromagnetic radiation from source 46 is then directed through passages 48 and 50 of elements 22 and 24, or simply directed through passage 82 of fence 70 of embodiment 10B. After interaction with the components in a liquid medium 18, electromagnetic radiation is passed from bag 14 to detector 66 for analysis by a suitable software program in conjunction with a personal computer. Where bag 14 is collapsed by fences 22 and 24, electromagnetic radiation may be passed through bag 14 to obtain a reference reading for use with spectral analyses of liquid in bag 14.

This spectroscopic method and apparatus of the present invention is capable of identifying and measuring many components in a liquid medium 18. Colorless materials, such as parenteral nutrients have distinctive spectral characteristics in regions outside the visible electromagnetic spectrum (400–700 nm). In particular, infrared (3000–25,000 nm) regions of the electromagnetic spectrum produces distinctive spectral features arising from specific molecular structures that are characteristics of the compounds. Such features derive from molecular vibrations of bonded atoms such as oxygen-hydrogen, carbon-hydrogen, nitrogen-hydrogen, and oxygen-carbon. Different types of carbon-hydrogen bonds can be distinguished, such as those arising from terminal C—H groups or $CH_3$ groups, i.e., fundamental molecular vibrations. Similar features occur at multiples of these fundamental frequencies (i.e., shorter wavelengths) and, hence, commonly occurred in the near-infrared. These are referred to as vibrational overtones such as the first and second overtones of carbon-hydrogen near 1700 and 1100 nm, respectively. Several different fundamental vibrations can combine to form a vibrational absorption at shorter wavelengths called a combination mode, ie., such as oxygen and hydrogen in molecular water near 1900 nm. Therefore, many regions of the electromagnetic spectrum may be used to obtain useful spectral data.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention. Further description of the invention is contained in the following examples.

The following examples are described in detail herein for the purpose of illustration of the present invention, but are not deemed to limit the scope of the invention herein.

EXAMPLE 1

The near infrared spectra of several parental nutrient compounds, i.e., water, 70% dextrose injection USP and 10% Travasol amino acid injection was measured individually or in various combinations to illustrate spectral characteristics. Such compounds formed an optically clear solution, which was placed in a fused quartz cuvette having an optical path of one (1) millimeter. The spectral data were acquired with a germanium detector found in a spectrophotometer, Model 200, manufactured by Guided Wave, Inc. of El Dorado Hills, Calif. Two (2) one meter long, 500 micron core diameter, silica-clad low-OH optical fibers and collimating lenses were connected to the spectrophotometer. Collimating lenses were placed between one end of each fiber and the cuvette. One fiber transmitted light from the tungsten light source inside the spectrophotometer through collimating lens and cuvette. The second collimating lens received light passing through the cuvette and focused the light into the second fiber, which transmitted the light back to the monochrometer and detector in the spectrophotometer. The absorbance characteristics obtained are charted in FIG. 4. Water reaches a maximum absorbance between 1400 and 1500 nanometers. The remaining components produce additional changes on the long wavelength side of the main water peak in the 1500–1800 nanometer region in FIG. 4.

EXAMPLE 2

Figure 5:
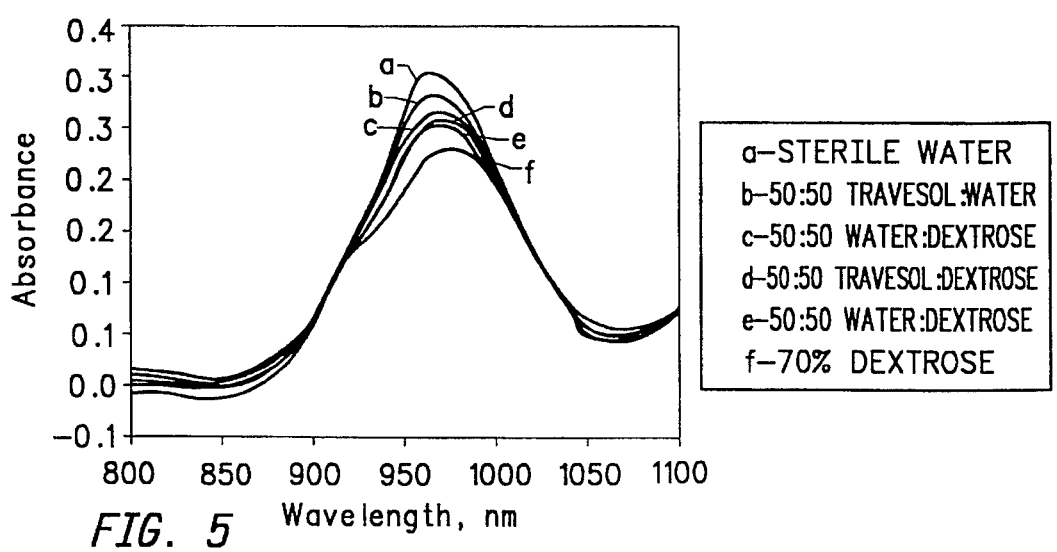
FIG. 5 is a graphical representation of the experimental results described in Example 2.

A polyvinyl chloride bag used for intravenous feeding (IV bag) was filled with sterile water, 70% dextrose injection, USP, and 10% Travasol amino acid injection, which are typical parenteral nutrients. These components formed an optically clear solution. Utilizing the apparatus shown in FIG. 1, spectral data were attained with a germanium detector found in a spectrophotometer distributed by Guided Wave, Inc. under the designation model 200. A pair of one meter long, 500 micron core diameter, silica-clad low-OH optical fiber and collimating lenses were employed with the subject detector. The IV bag was compressed to an optical path of 15 millimeters. Distinguishing characteristics were uncovered in the compounds within the I.V. bag in the 800 to 1100 nanometer region of an electromagnetic source of radiation. Reference analysis was also performed on an empty I.V. bag. FIG. 5 represents the results of this analysis.

EXAMPLE 3

Figure 6:
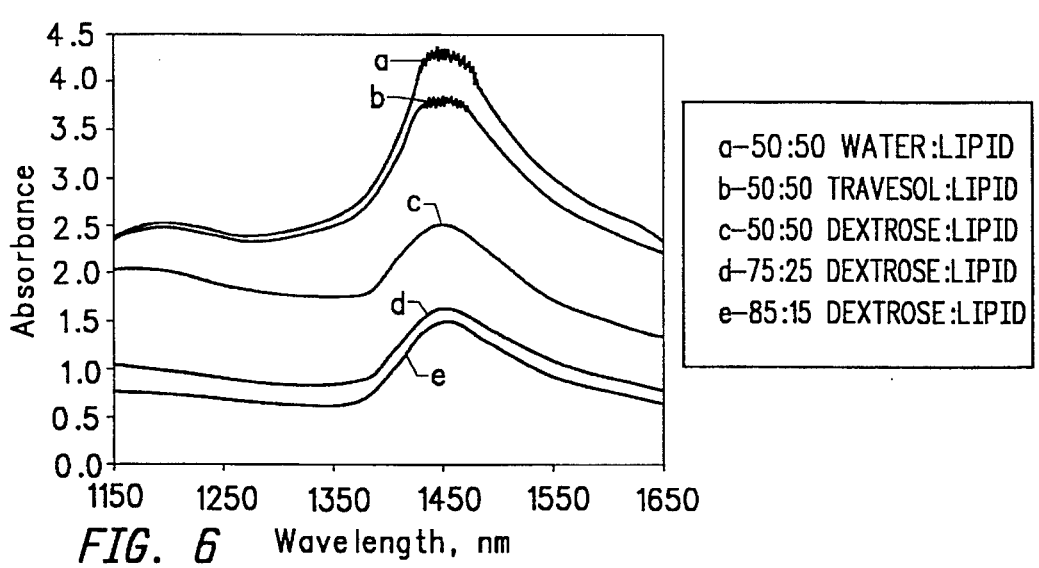
FIG. 6 is a graphical representation of experimental results described in Example 3.

The parenteral compounds of Examples 1 and 2 were placed in an I.V. bag with the addition of a common 20% Intralipid intravenous fat emulsion (I.V. fat emulsion). The final mixture of nutrients included fat compounds occupying less than 50% of the volume of the I.V. bag mixture. FIG. 6 shows that, in spite of the light scattering characteristics of the milky solution found in the IV bag containing the fat compounds, transmission may still be performed, through 1–2 millimeters of an optical path of the bag. In other words, the bag shown in FIG. 6 represents a squeezing of the bag to a smaller optical path, (1.5 to 2 millimeters) than the optical path represented in FIG. 5. It is estimated that 95% of the light passed through the bag in this Example was scattered and lost: through the first millimeter of the optical path. Various mixtures of 70% dextrose injection USP, 20% Intralipid I.V. fat emulsion, 10% Travasol, and water are employed and are identified on FIG. 6. The absorbance characteristics are clearly identifiable for each mixture in which changes in the intensity of the water peak near 1450 nm, effects due to amino acids and dextrose in the 1500–1700 nm region, and contribution from lipid near 1200 m are identifiable. As will be shown from diffuse reflectance spectral data hereinafter in Example 4, these features can be used to perform quantitative analysis of the mixtures in the bag.

EXAMPLE 4

Figure 7:
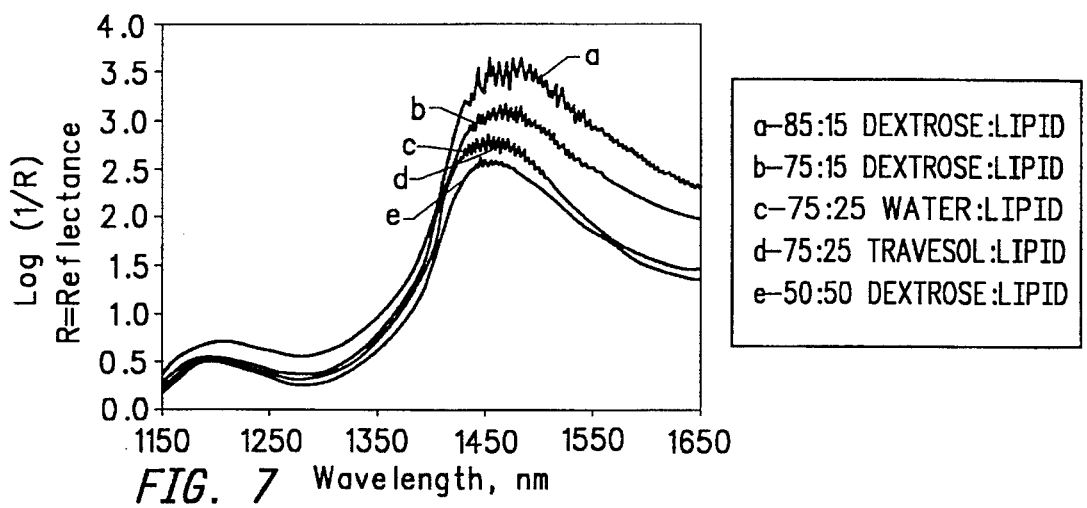
FIG. 7 is a graphical representation of an experimental result described in Example 4.

The apparatus shown in FIG. 3 was employed to conduct diffuse reflectant/transmittance measurements through I.V. bags constructed of polyvinyl chloride (PVC) filled with mixtures of parenteral nutrients. The mixtures were composed of 20% Intralipid I.V. fat emulsion, 10% Travasol (amino acid injection solution), 70% dextrose injection solution, and sterile water. Nutrients were measured volumetrically with a graduated cylinder mixed, and placed in one (1) liter PVC I.V. bags. The device depicted in FIG. 3 was set to provide an optical path, excluding the thickness of the I.V. bag material, of about 15 millimeters through the solution in the filled I.V. bag. The set screw spacer means 12, FIG. 1, was employed to compress the bag to this particular optical path setting. Since these mixtures all contained lipid and hence, scattered light suitable for diffuse reflectance measurements, the space set for the optical path was not critical to the measurement. A spectrophotometer was employed, similar to the spectrophotometer utilized in Example 1 using an InGaAs detector. The source of light was a tungsten lamp. The light was delivered through a 6 mm dia. hole in a white Spectralon block available from Labsphere, Inc., North Sutton, N.H. from a 20 watt tungsten source. This block was attached to the stationary fence 70 in FIG. 3. A bundle of 10 individual fibers of the type described in Example 1 were cemented into a small metal fitting and inserted through the Spectralon block at 30 degrees to the hole containing the tungsten light source. The end of the fiber bundle fitting was coincident with the end of the block in contact with the IV bag. Near infrared spectra were collected between 1100 and 1650 nanometers. FIG. 7 depicts the results obtained where the various mixtures used were clearly recognizable, with the exception of the 75:25 Travasol and lipid mixture, which, generally, is only slightly different from the 75:25 water and lipid mixture.

Figure 8:
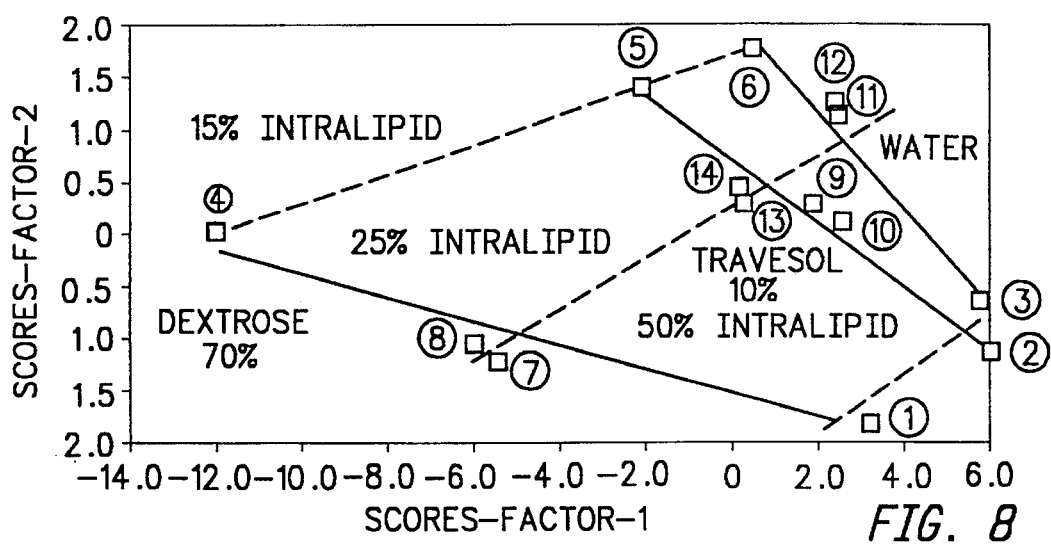
FIG. 8 is a graphical representation of PCA plot of scores described in Example 5.

The spectral differences shown in FIG. 7 can be quantified with the commonly used method of Principal Component Analysis (PCA). PCA is essentially a pattern recognition procedure that can assign one number to the entire spectrum employed in the analysis. PCA is accomplished by analyzing all spectral data of all samples in determining the linear combination of data that explains the largest variation of spectral information. A different linear combination is next determined that shows the next largest variation in the spectral data. The linear combinations are determined in this way. Each linear combination is referred to as a FACTOR which provides co-efficient that multiply the data at each wavelength. The product of this multiplication is summed to determine one number which is referred to as a SCORE. Thus, by plotting SCORES from FACTOR I against those from FACTOR II, samples can be distinguished or identified. In mathematical terms, FACTORS are a set of orthogonal eigenvectors whose lengths represent the percentage of variation in spectral data. SCORES are obtained by multiplying the elements of each eigenvector, referred to as a LOADING (each of which is a co-efficient for the spectral data at a specific wavelength) times the absorbance at that wavelength, and summing the results. Essentially, each sample is projected on each eigenvector and the distance from the origin i.e., the intersection of all eigenvectors is thus measured. Other mathematical methods exist for the purposes of identification of data, including the computation of direction cosines, factor analysis, and cluster analysis. Referring to FIG. 8, a PCA plot is illustrated using SCORES from the first two FACTORS of the diffuse reflectance data from the samples presented in FIG. 7. Table 1 herein represents the volume fraction of the nutrients employed in the preparation of FIG. 8:

TABLE I

| SAMPLE | 10% TRAVASOL | STERILE WATER | 70% DEXTROSE | 20% INTRALIPID |
|---|---|---|---|---|
| 1 |  |  | 0.50 | 0.50 |
| 2 | 0.50 |  |  | 0.50 |
| 3 |  | 0.50 |  | 0.50 |
| 4 |  |  | 0.85 | 0.15 |
| 5 | 0.85 |  |  | 0.15 |
| 6 |  | 0.85 |  | 0.15 |
| 7 |  |  | 0.75 | 0.25 |
| 8 |  |  | 0.75 | 0.25 |
| 9 | 0.75 |  |  | 0.25 |
| 10 | 0.75 |  |  | 0.25 |
| 11 |  | 0.75 |  | 0.25 |
| 12 |  | 0.75 |  | 0.25 |
| 13 | 0.25 | 0.25 | 0.25 | 0.25 |
| 14 | 0.25 | 0.25 | 0.25 | 0.25 |

These two factors account for 97% of the spectral variation among all of the samples, each identified by a sample number with a circle around the same. The 70% dextrose injection USP, water, and 10% Travasol amino acid injection components are clearly distinguished by the solid lines of FIG. 8. The 20% intralipid fat emulsion content is also clearly shown by the three dashed lines representing 15%, 25%, and 50% intralipid. The solid Travasol and water lines lie closer to one another, but are significantly spaced from the dextrose line in FIG. 8. Such a relationship corresponds to spectral data in which water and Travasol are more similar to each other than dextrose. Repeated measurements on the same IV bag showed reasonable reproducibility, i.e., samples 7 and 8 and samples 11 and 12 of FIG. 8.

Figure 9:
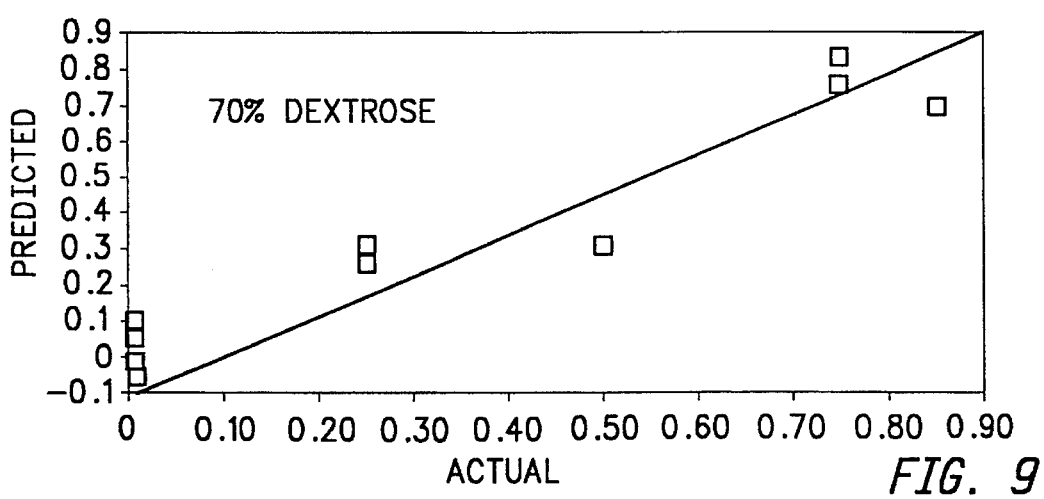
FIGS. 9 and 10 are graphical representations depicting predictions using PLS analysis described in Example 4.
Figure 10:
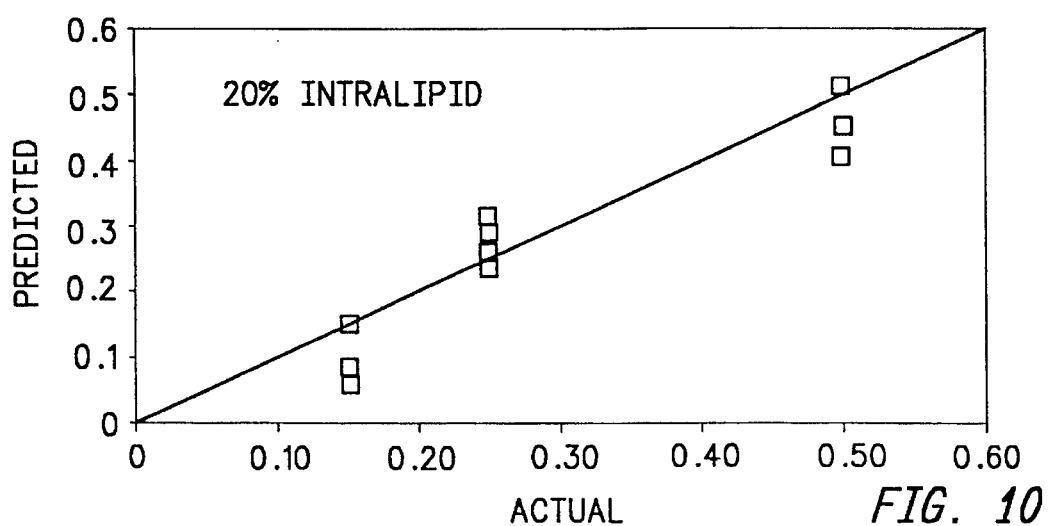

Partial-Least Squares (PLS) method was also employed in the diffuse reflectance method for the samples shown in FIG. 8. The results of this method are shown in FIGS. 9–10 of the present invention. Partial-Least Squares (PLS) multivariate procedure is commonly used to determine chemical or physical property information from spectral data. Computer programs such as UNSCRAMBLER are available from Camo of Norway. SPECTRACALC, and GRAMS/386 are available from Galactic Industries, Inc., of Salem, N.H. Pirouette is available from Infometrics of Redmond, Wash. GRAMS/386 was used in the present analysis with a personal computer. PLS incorporates the benefits of PCA and attempts to provide a model of the data with as few a number of FACTORS as is needed. A six FACTOR PLS model of the diffuse reflectance data of Table I represents a strong indication that mixtures in IV bags can be analyzed non-invasively. FIGS. 9 and 10 show predictions of 70% dextrose injection and 20% intralipid IV fat emulsion.

Figure 11:
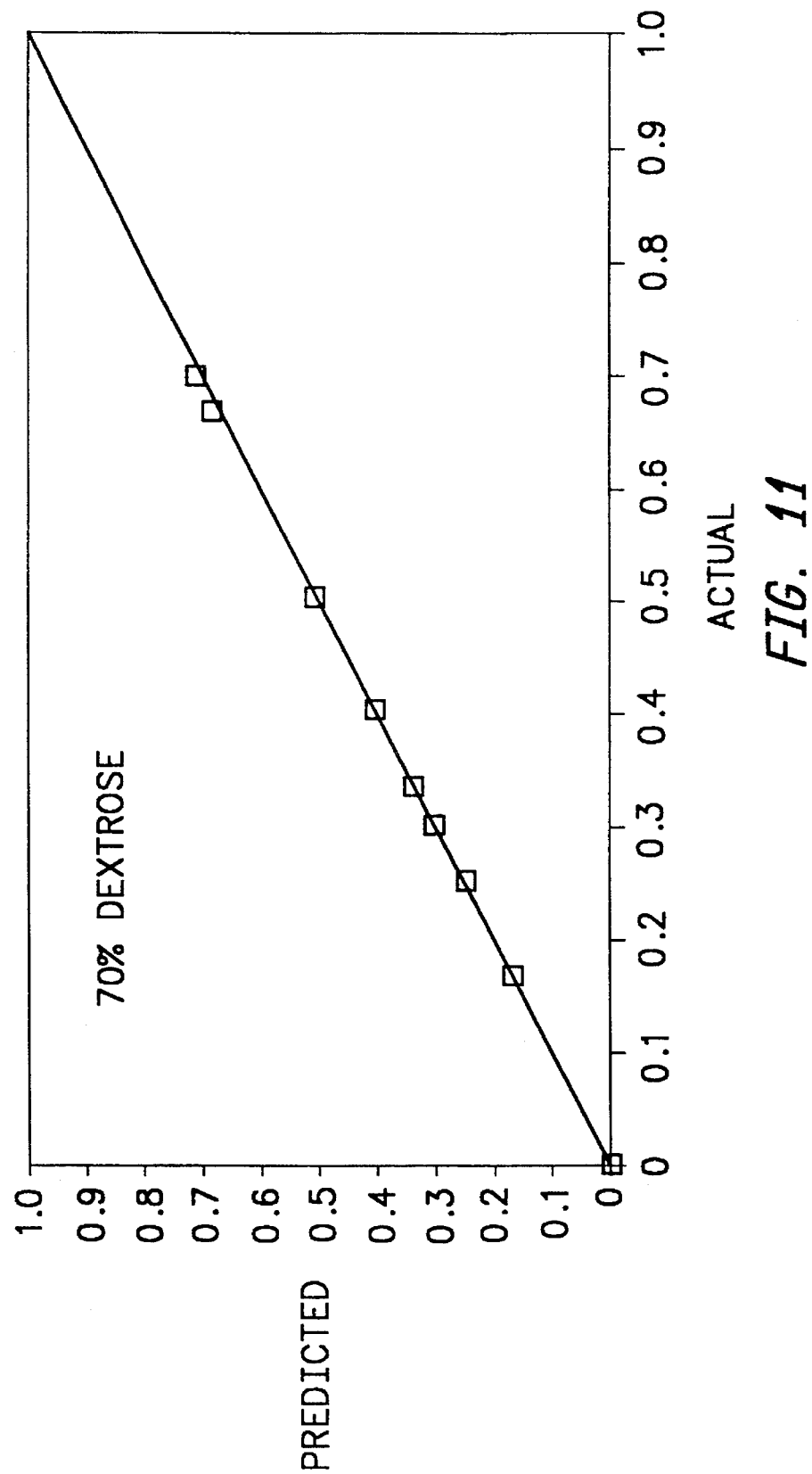
FIG. 11 is a graphical representation of a PLS model utilizing data found in Example 4.

PLS analysis of the one millimeter optical path using transmission through cuvettes, shown in FIG. 4 for samples without fat emulsion, also produced excellent quantitative results. The prediction for 70% dextrose injection USP in the mixture from a five FACTOR PLS model as presented in FIG. 11. The standard error of calibration for the sample set was 5%. The PLS, model in FIG. 11 utilized all spectral information from all samples as seen in FIG. 4.

Figure 12:
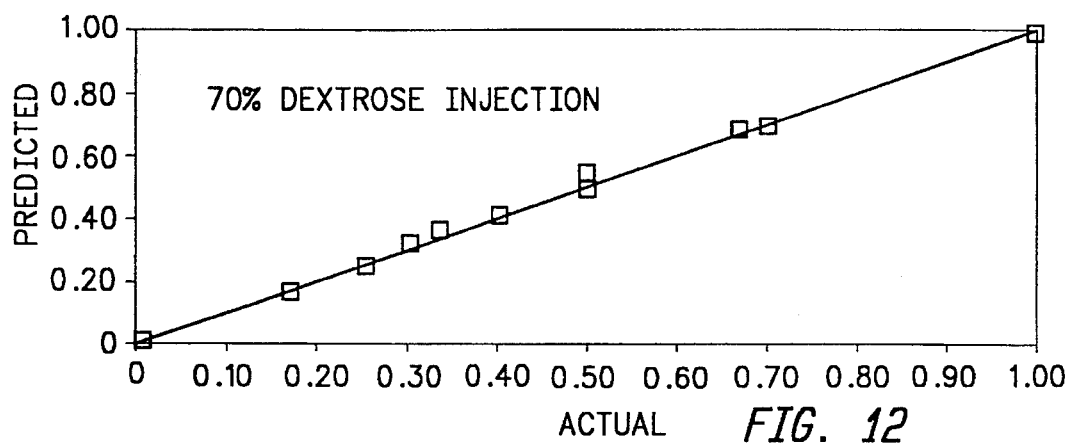
FIGS. 12, 13, and 14, are graphical representations of MLR methods applied to the data shown in Table 2 of Example 4.
Figure 13:
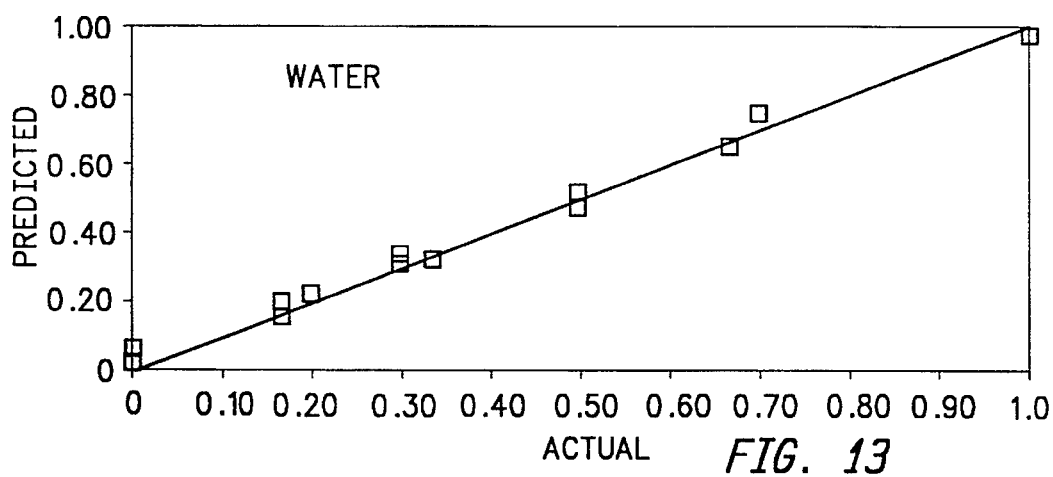
Figure 14:
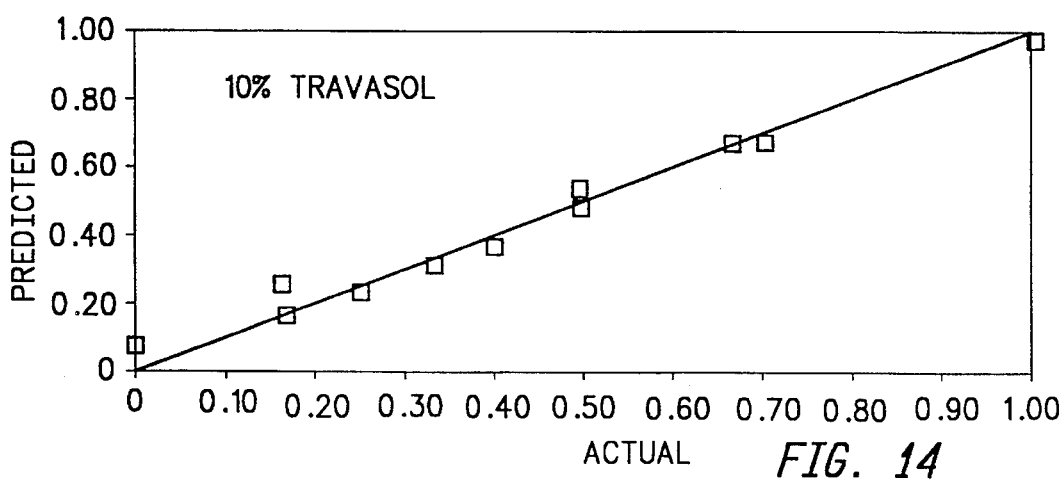

Since it is often desirable to use a simple system comprising only a few wave lengths for quantitative analysis, a multi linear Regression Method (MLR) can also be used to predict physical properties of liquids and solids and analyze mixtures from near infrared spectra. MLR was performed on the one millimeter transmission spectra shown in FIG. 4. The result in calibration are presented in FIGS. 12, 13, and 14, for 70% dextrose injection USP, sterile water, and 10% Travasol amino acid injection, respectively. The data were generated by employing 2, 3, and 5 wavelengths between 1100 and 1800 nanometers, respectively. This data are shown in Table 2 as follows:

TABLE II

| SAMPLE | 70% DEXTROSE | | WATER | | 10% TRAVASOL | |
|---|---|---|---|---|---|---|
|  | ACT. | PRED. | ACT. | PRED. | ACT. | PRED. |
| 1 | 0.000 | 0.007 | 0.000 | 0.014 | 1.000 | 1.003 |
| 2 | 0.000 | −0.005 | 1.000 | 0.977 | 0.000 | 0.072 |
| 3 | 1.000 | 0.986 | 0.000 | −0.041 | 0.000 | −0.061 |
| 4 | 0.000 | 0.008 | 0.500 | 0.468 | 0.500 | 0.475 |
| 5 | 0.500 | 0.522 | 0.500 | 0.517 | 0.000 | −0.063 |
| 6 | 0.500 | 0.489 | 0.000 | 0.038 | 0.500 | 0.524 |
| 7 | 0.333 | 0.344 | 0.333 | 0.310 | 0.333 | 0.307 |
| 8 | 0.667 | 0.681 | 0.166 | 0.128 | 0.166 | 0.241 |
| 9 | 0.166 | 0.156 | 0.166 | 0.198 | 0.667 | 0.675 |
| 10 | 0.166 | 0.162 | 0.667 | 0.653 | 0.167 | 0.149 |
| 11 | 0.700 | 0.697 | 0.300 | 0.306 | 0.000 | 0.052 |
| 12 | 0.250 | 0.240 | 0.500 | 0.488 | 0.250 | 0.219 |
| 13 | 0.300 | 0.308 | 0.700 | 0.747 | 0.000 | 0.057 |
| 14 | 0.400 | 0.399 | 0.200 | 0.209 | 0.400 | 0.352 |
| 15 | 0.000 | −0.007 | 0.300 | 0.320 | 0.700 | 0.683 |

| Wavelength, nm | Coeff. | Waveln. | Coeff. | Waveln. | Coeff. |
|---|---|---|---|---|---|
| 1566 | 16.21 | 1528 | 3.5355 | 1533 | −51.3572 |
| 1716 | −5.3741 | 1716 | −104.7859 | 1778 | 56.0781 |
| Offset | −4.9432 | 1744 | 98.6863 | 1287 | 194.9018 |
| Mult. R | 0.99378 | Offset | −3.4804 | 1193 | −668.3302 |
|  |  | Mult. R | 0.99521 | 1194 | 455.3483 |
| SEC | 0.0347 | SEC | 0.0306 | Offset | 9.8891 |
|  |  |  |  | Mult.R | 0.98888 |
|  |  |  |  | SEC | 0.0548 |

As may be observed, wavelengths of 1566 and 1716 nanometers were employed for dextrose. The wavelengths employed for water and Travasol are also shown on Table 2. The indication is that a simpler and less expensive system having several discrete detectors, each covered by a narrow wavelength filter or a device having means to switch between several discrete wavelengths, could be built to quantitatively predict the composition of mixtures as these shown in FIG. 4.

Figure 15:
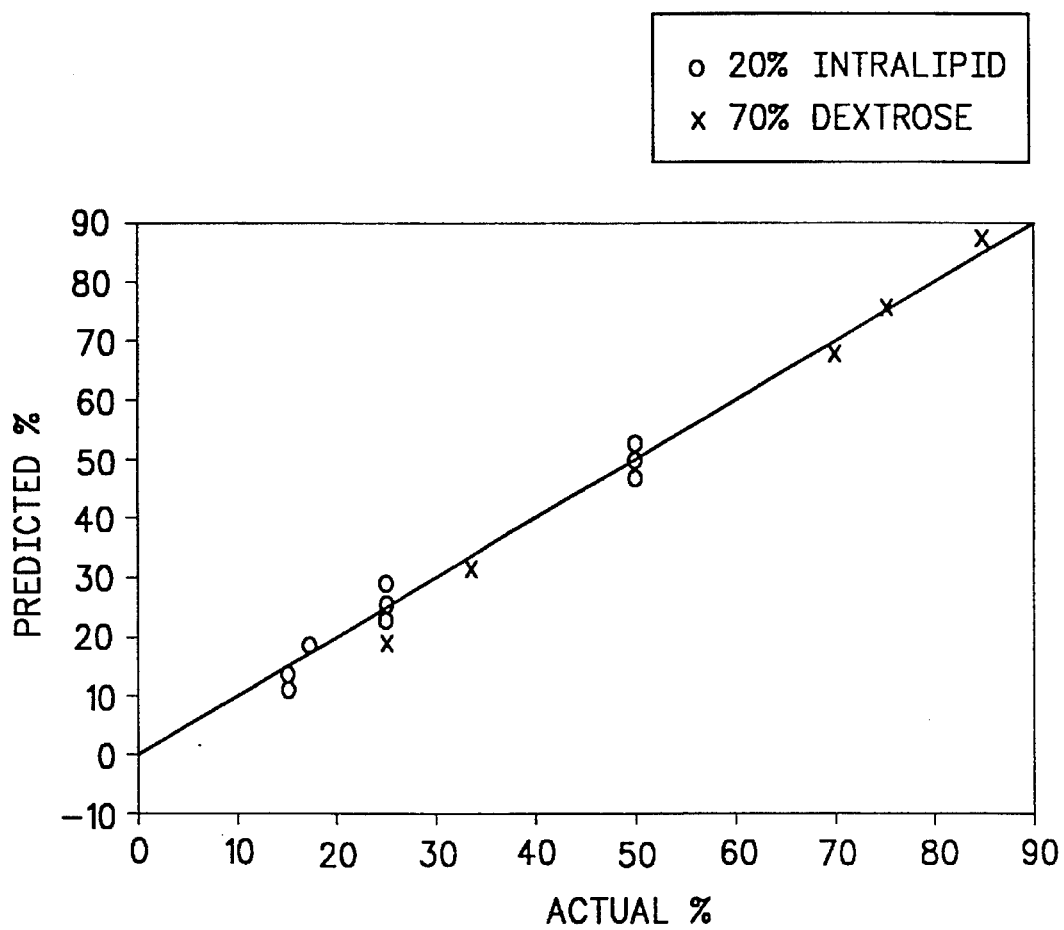
FIG. 15 is a graphical representation of a step wise MLR program utilizing the data of Table 1 of Example 4.

A stepwise multiple linear regression program was also used to determine a small set of wavelengths which could be used to predict the intralipid and 70% dextrose mixture in IV bags filled with the samples identified in Table II, analyzed by the embodiment of 10A of FIG. 1 (transmittance). The optical path was set to a distance of approximately 1.6 mm. Actual versus predicted values were plotted as shown on FIG. 15. It should be noted that a perfect calibration would plot on the diagonal line found in FIG. 15. Three (3) and five (5) wavelengths were used to produce excellent fits with standard errors of prediction of 2.1 and 3.7% for the 20% intralipid component and the 70% dextrose component in the mixture, respectively. The three (3) wavelengths used for the 20% intralipid were 1606, 1536, and 1532 nanometers which are listed in decreasing order of importance. Similarly, the five (5) lengths employed for the 70% dextrose were 1414, 1610, 1212, 1424, and 1200 nanometers, also listed in order of importance. Each mathematical solution also included a constant term.

What is claimed is:

1. An apparatus for measuring a component in a liquid medium within the chamber of a flexible translucent container formed by a wall portion, comprising:
    a. spacer means for sequentially determining a plurality of optical paths across the container wall portion and chamber, and the flexible translucent container wall portion alone, said spacer means including a passage for electromagnetic radiation; and
    b. a source of electromagnetic radiation capable of directing electromagnetic radiation through said spacer means passage, through the wall portion of the container, and along any of said determined optical paths, said source of electromagnetic radiation being capable of interaction with a component in the bag chamber and the wall portion of the bag; and
    c. detector means for analyzing said electromagnetic radiation after interaction with the components in the flexible translucent container chamber and the wall portion of the bag.

2. The apparatus of claim 1 in which said spacer means includes a pair of elements placed in opposition to one another, at least one of said elements including a passage for electromagnetic radiation to the wall portion of the bag.

3. The apparatus of claim 2 in which additionally comprises adjustment means for establishing the distance between said pair of elements.

4. The apparatus of claim 3 in which said adjustment means includes a threaded member spanning said pair of elements, said threaded member threadingly engaging one of said elements to effect movement said one of said elements thereby, and a guide for confining movement of said one of said elements to a predefined direction.

5. The apparatus of claim 4 in which said guide includes a pair of elongated elements extending between said pair of elements.

6. The apparatus of claim 1 which additionally includes a fiber optic conduit for transporting electromagnetic radiation from said source of electromagnetic radiation to said spacer means passage.

7. The apparatus of claim 6 which additionally includes a fiber optic conduit for transporting electromagnetic radiation from said spacer means to said detector means.

8. The apparatus of claim 2 which additionally comprises a reflector located at one of said pair of elements, said reflector being located to reflect electromagnetic radiation, passed through the chamber of the flexible translucent bag back through the chamber of the flexible translucent bag.

9. The apparatus of claim 1 in which said source of electromagnetic radiation emanates electromagnetic radiation in the near-infrared region of the electromagnetic spectrum.

10. The apparatus of claim 1 which additionally includes at least one wavelength filter placed between said source of electromagnetic radiation and said detector means.

11. The apparatus of 10 which additionally includes a lens placed between said source of electromagnetic radiation and said detector means.

12. A method of analyzing components in a liquid medium within the chamber of a flexible bag comprising the steps of:
    a. placing the bag in spacer means for determining the optical path across the bag chamber, said spacer means including a passage for electromagnetic radiation;
    b. directing electromagnetic radiation from a source of electromagnetic radiation to the components in said bag chamber for interaction therewith; and
    c. analyzing said electromagnetic radiation with detector means after interaction of said electromagnetic radiation with the components in the bag chamber.

13. The method of claim 12 in which said step of analyzing said electromagnetic radiation further includes the step of analyzing electromagnetic radiation transmitted through said components in the bag chamber.

14. The method of claim 12 in which said step of analyzing said electromagnetic radiation further includes the step of analyzing electromagnetic radiation reflected from said components in the flexible bag.

15. The method of claim 12 in which said step of analyzing said electromagnetic radiation further includes the step of analyzing electromagnetic radiation transmitted through and reflected back through components in the bag chamber.

16. The method of claim 12 which further comprises the step of passing electromagnetic radiation through the flexible bag alone in order to obtain a reference spectrum.

17. The method of claim 16 which further comprises the step of expelling the liquid medium from the flexible bag prior to said step of passing electromagnetic radiation through the flexible bag alone.

18. The method of claim 16 in which said step of placing the bag in spacer means for determining the optical path across the bag chamber is a first optical path and further includes the step of placing the bag in said spacer means for determining a second optical path across the bag chamber; directing electromagnetic radiation to the components in said chamber for interaction therewith; and analyzing said electromagnetic radiation with said detector means after interaction of said electromagnetic radiation with the components in the bag chamber.

19. The method of claim 12 in which said components are parenteral and enteral nutrients.

20. An apparatus for detecting light scattering components in a liquid medium within the chamber of a flexible translucent bag formed by a wall portion, comprising:
    a. a fence element, said fence element including a passage for electromagnetic radiation to the wall portion of the bag, said fence element further determining the optical path across the flexible translucent bag chamber;
    b. a source of electromagnetic radiation capable of directing electromagnetic radiation through said fence element passage, said source of electromagnetic radiation being capable of interaction with a component in the bag chamber and the wall portion of the bag; and
    c. detector means for analyzing said electromagnetic radiation after interaction with the components in the bag chamber and the wall portion of the bag, said detector means receiving said electromagnetic radiation, after interaction with a component in the bag chamber, through said fence passage.

21. An apparatus for non-invasively identifying components in a liquid medium within an interior of a flexible bag, the apparatus comprising:

a. a source of electromagnetic radiation capable of directing electromagnetic radiation into the interior of the bag, the source of electromagnetic radiation capable of interaction with the components in the bag chamber and the bag;

b. means for defining the optical path that the electromagnetic radiation travels across the interior of the bag;

c. optical detector means located outside the bag receiving the electromagnetic radiation after interaction with the components in the bag chamber interior and the wall portion of the bag, and providing a signal indicative thereof; and d. means for analyzing the signal to identify the components of the liquid medium in the bag.

* * * * *